(12) United States Patent
Christofano

(10) Patent No.: US 12,144,952 B1
(45) Date of Patent: Nov. 19, 2024

(54) TATTOO MACHINE ASSEMBLY

(71) Applicant: Nick Christofano, Greenburg, PA (US)

(72) Inventor: Nick Christofano, Greenburg, PA (US)

( * ) Notice: Subject to any disclaimer, the term of this patent is extended or adjusted under 35 U.S.C. 154(b) by 330 days.

(21) Appl. No.: 17/697,377

(22) Filed: Mar. 17, 2022

Related U.S. Application Data

(60) Provisional application No. 63/228,930, filed on Aug. 3, 2021.

(51) Int. Cl.
*A61M 37/00* (2006.01)

(52) U.S. Cl.
CPC .............................. *A61M 37/0076* (2013.01)

(58) Field of Classification Search
CPC .. A61M 37/0076; A01K 11/00; A01K 11/005; A61B 17/205
See application file for complete search history.

(56) References Cited

U.S. PATENT DOCUMENTS

| | | | | |
|---|---|---|---|---|
| 5,551,319 A | * | 9/1996 | Spaulding | B43K 8/22 |
| | | | | 30/362 |
| 9,393,395 B2 | * | 7/2016 | Miller | A61M 37/0076 |
| 2016/0263365 A1 | * | 9/2016 | Smith | A61M 37/0076 |
| 2022/0387773 A1 | * | 12/2022 | Petz | A61M 37/0076 |

* cited by examiner

*Primary Examiner* — David B. Thomas
(74) *Attorney, Agent, or Firm* — Richard K Thomson

(57) ABSTRACT

An improvement to a tattoo machine assembly consists of a bifurcated armature bar which has a steel plate spring secured to the two halves of the armature bar to allow the artist to vary the spring rate afforded the armature bar and the tattoo needle secured thereto by switching out the steel plate spring for a different steel plate spring having a different plate thickness and, therefore, a different spring rate.

2 Claims, 5 Drawing Sheets

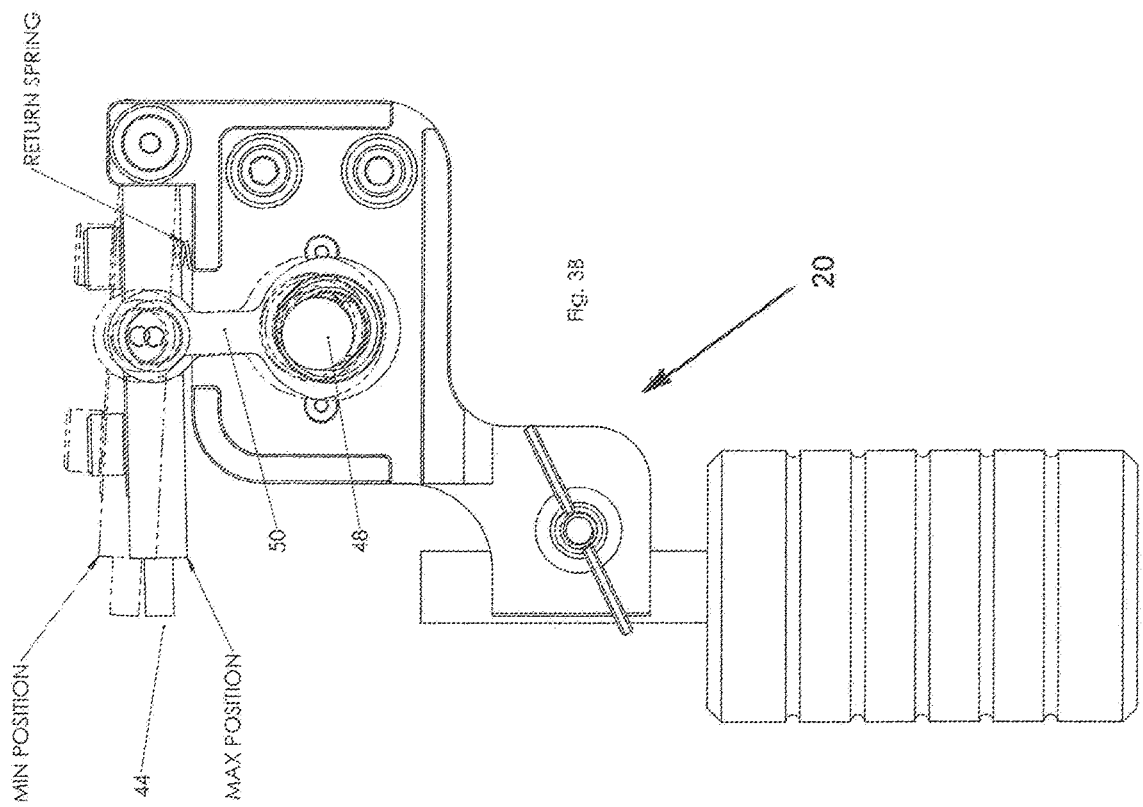
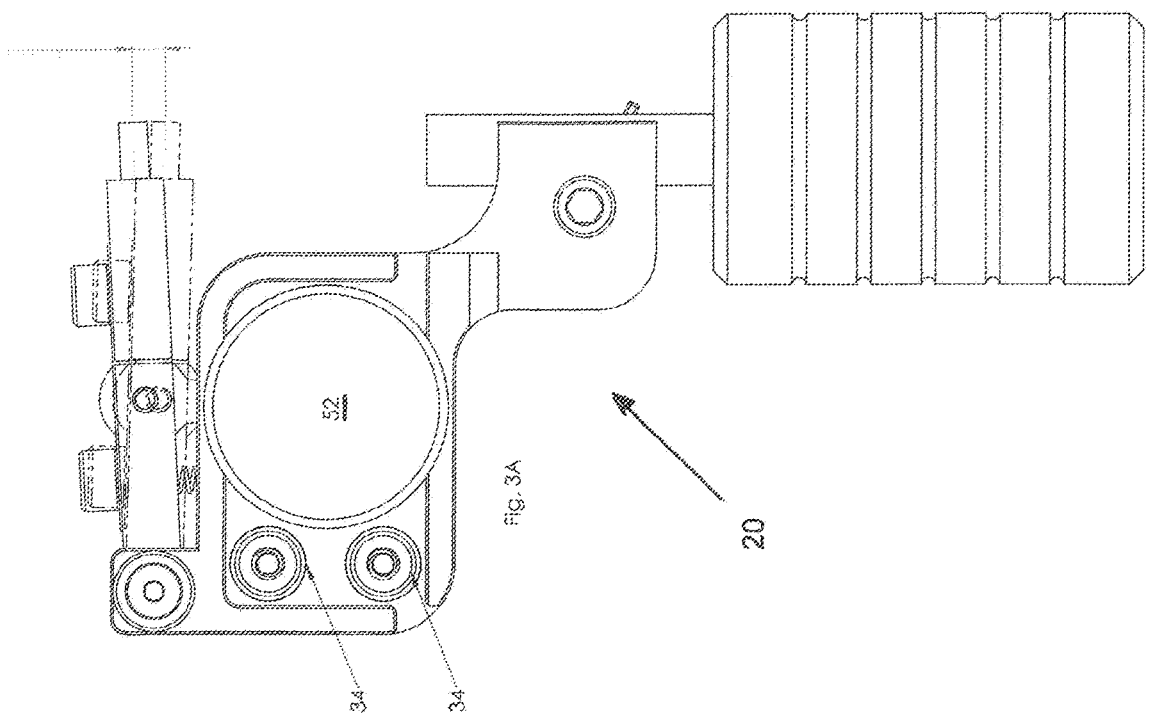

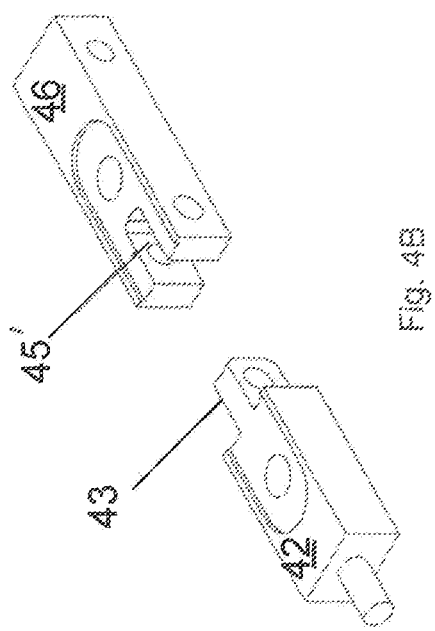
Fig. 4B
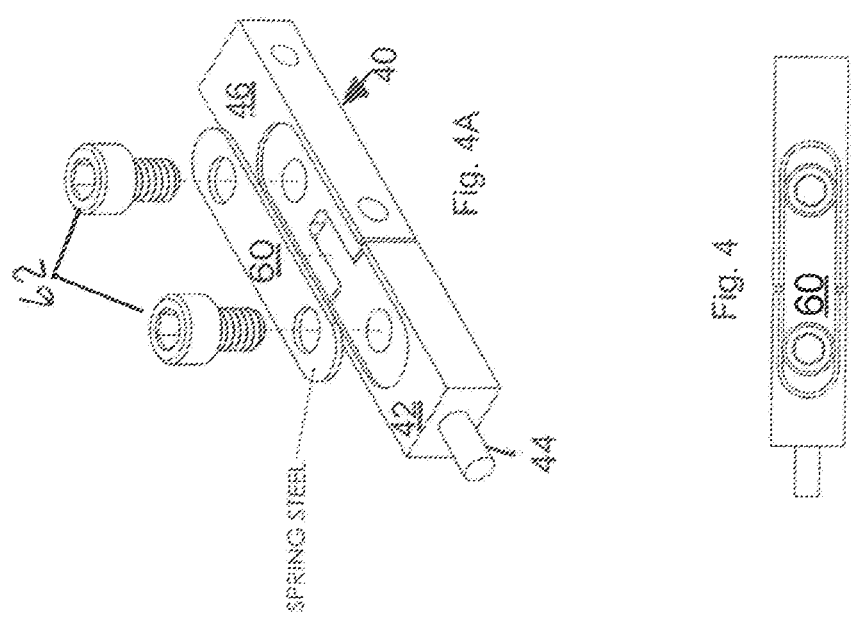

TATTOO MACHINE ASSEMBLY

BACKGROUND AND SUMMARY OF THE INVENTION

The present invention is directed to the field of body art. More particularly, the present invention is directed to rotary tattoo machine assembly with adjustable dampening.

It will be obvious that the field of body art involves a great deal of personal taste. This is true not only for the person receiving the imprint, but also for the artist herself/himself. The touch of the inking pen is a key feature for determining the artistry of the finished product. Accordingly, the present design gives the artist/operator the ability to adjust the "feel" of the machine by using various thicknesses of spring steel that are interchangeable, hence, adjusting the dampening aspect per the operator's/artist's specific preference. This also provides an adjustability level for different areas of the body part letting the machine strike strongly or delicately per the artist's preference as the artist deems necessary for that specific body part/skin thickness. The variability afforded the dampening of this machine is what makes the application of pigment to the skin highly efficient with the least amount of trauma to the skin; furthermore, by reducing the amount of force required to implant the ink, a quicker heal time is afforded to recover from the impact to the skin.

It is the intention of this development to design a consistent tool that still retained a traditional-esque feel and sound of a coil/relay machine. The positive feel in the skin that a coil machine provides has always been the inventor's preference. However, the consistency of a rotary driven machine is difficult to dispute. This design provides a give/bog as the needle strikes the skin, much like a coil machine. The "perfect punch" every artist is looking for, with all the reliability and efficiency that a rotary driven machine is known for, is provided by this innovation, spinning exactly the same, every time. That consistency is paired with the ability to dampen/slow down the needle speed as it comes in contact with the skin, before retracting and completing its stroke. This is what makes depositing pigment highly efficient. It essentially slows needle speed down just enough before retraction, giving the needle more time in the skin to do it's job. More time in the skin depositing pigment will likely result in higher saturation with the least amount of passes. The least amount of trauma inflicted to reach saturation will produce better healing tattoos.

While the "dampening" term to describe this action, but it is also just as easy to think about the actuation of this device in terms of a suspension circuit: slow or fast, soft or hard. What speed and force is needed to actuate the device is the approach used in tuning and explaining this give or bog. This action is also directly affected by rubber bands, needle bar tension, pigment viscosity; anything that would potentially restrict that movement is considered. A stronger spring will require more force to actuate and provides a more rigid connection. A more rigid connection will be put back to its start position quicker in comparison to that of a softer connection, because there is no excessive movement in that connection. In other words it does not flex as much as a softer spring. That rigidity directly affects the retraction of the machine to its start position (on a rotary driven machine). A coil machine utilizes spring steel for its retraction, where as a rotary driven machine is put back to its start position under the power of the motor. The design of the present device enables the artist to delay that retraction to its start position, with an element of tune-ability by way of various spring steel thicknesses. It differs from most conventional/hybrid rotary machines in the sense that this spring directly affects the course of the machine's stroke in contrast to simply being a connection point. Coil machine feel, with rotary machine consistency.

The art of tattooing involves more than simply opening up the skin and depositing pigment; this device works efficiently because of its "order of operation" from the machine power source (regardless of type) to the tip of the needle. This design provides an alternative to the typical rigid connection from motor source to needle tip. Instead, an intermediate spring interrupts the normal operation, softening the strike and retarding the return stroke of the needle. As the needle comes in contact with the skin, the spring allows the needle to slow down slightly, enough to break the skin and deposit pigment/push pigment into the skin. It is more that just breaking the skin; the slowing down of the needle speed enables pigment to be deposited before retracting.

For that reason, a key feature of the present invention is a replaceable spring of plate steel, the thickness of which can vary between 0.020 and 0.050 inch which is secured between the two pivoted elements of the ink pen. By way of example and not limitation, the plates may vary by 0.005 inch between 0.020 and 0.050 inch (seven plates in all) to allow the tattoo machine assembly to be adapted to the feel of the tattoo artist and the variations in skin thickness/receptivity. The thickness of the plate varies the amount of dampening force provided to the pen/needle.

Various other features, advantages, and characteristics of the present invention will become apparent after a reading of the following detailed description.

BRIEF DESCRIPTION OF THE DRAWINGS

The preferred embodiment(s) of the present invention is/are described in conjunction with the associated drawings in which like features are indicated with like reference numerals and in which

FIG. 1A is a side view of the first embodiment;

FIG. 1B is a top view of the first embodiment;

FIG. 1C is a rear view of the first embodiment;

FIG. 3A is a right side schematic view of the first embodiment;

FIG. 3B is a left side schematic view of the first embodiment;

FIG. 4 is a top view of the armature bar of the first embodiment;

FIG. 4A is a partially exploded front perspective view of the armature bar shown in FIG. 4; and, FIG. 4B is an exploded front perspective view of the armature bar.

DETAILED DESCRIPTION OF THE PREFERRED EMBODIMENT(S)

Figure 1:
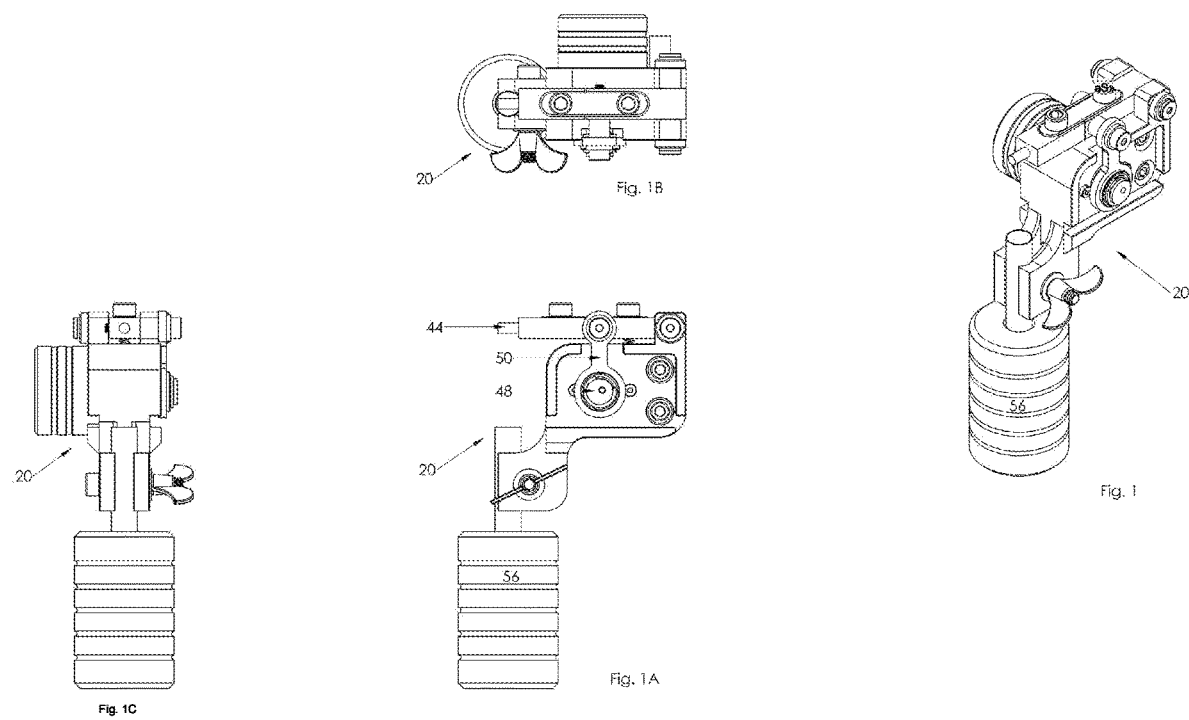
FIG. 1 is a side perspective view of the first embodiment of the tattoo machine assembly of the present invention.
Figure 2:
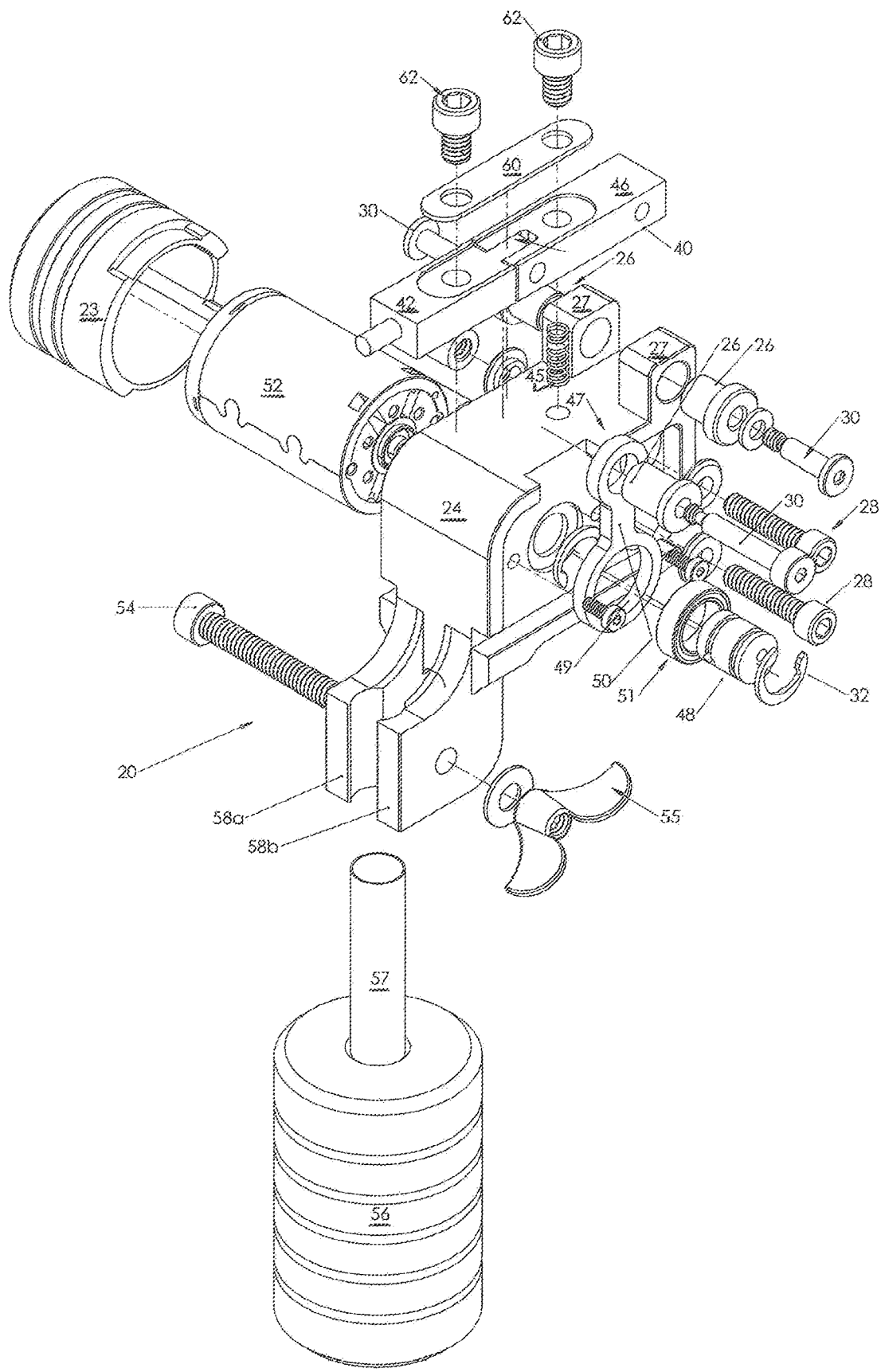
FIG. 2 is an exploded view of the first embodiment.

A first embodiment of the tattoo machine assembly of the present invention is depicted in FIGS. 1-2 generally at 20. Tattoo machine assembly 20 comprises a machine body or frame 24 to which is secured rotary motor 52 having a cover 23. Machine body 24 has a pair of vise arms 58a and 58b which grip tube 57 of hand grip 56 via vise bolt 54 and vise nut 55.

Armature bar 40 is bifurcated and protrusion/rib 43 is received in slot 45' of rear portion 46 and secured therein by pivot pin 54 (FIG. 4B). Since the depth of slot 45' exceeds the length of rib 43, a limited amount of pivotal motion is permitted. Two pivot-point sleeve bushings 26 pass through opposing cars 27 of machine frame 24 and are secured to rear portion 46 of armature bar 40 by bolts 30 while a third pivot-point bushing 26 extends through upper aperture 47 of connecting rod 50 and is secured to the midpoint of armature bar 40 by a third bolt 30. Return spring 45 reacts between the upper surface of machine frame 24 and the underside of rear portion 46 of armature bar 40 to push armature bar upwardly. Lower aperture 49 of connecting rod receives roller bearing 51 which supports offset flywheel 48 in aperture 49. C-clips 32 are received in grooves on either end of offset flywheel 48 to secure the assembly of parts 48, 49, 51. Two electrical connection binding posts 34 (positive and negative) are attached to the machine body 24 adjacent motor 52 (FIG. 3A).

Figure 3C:
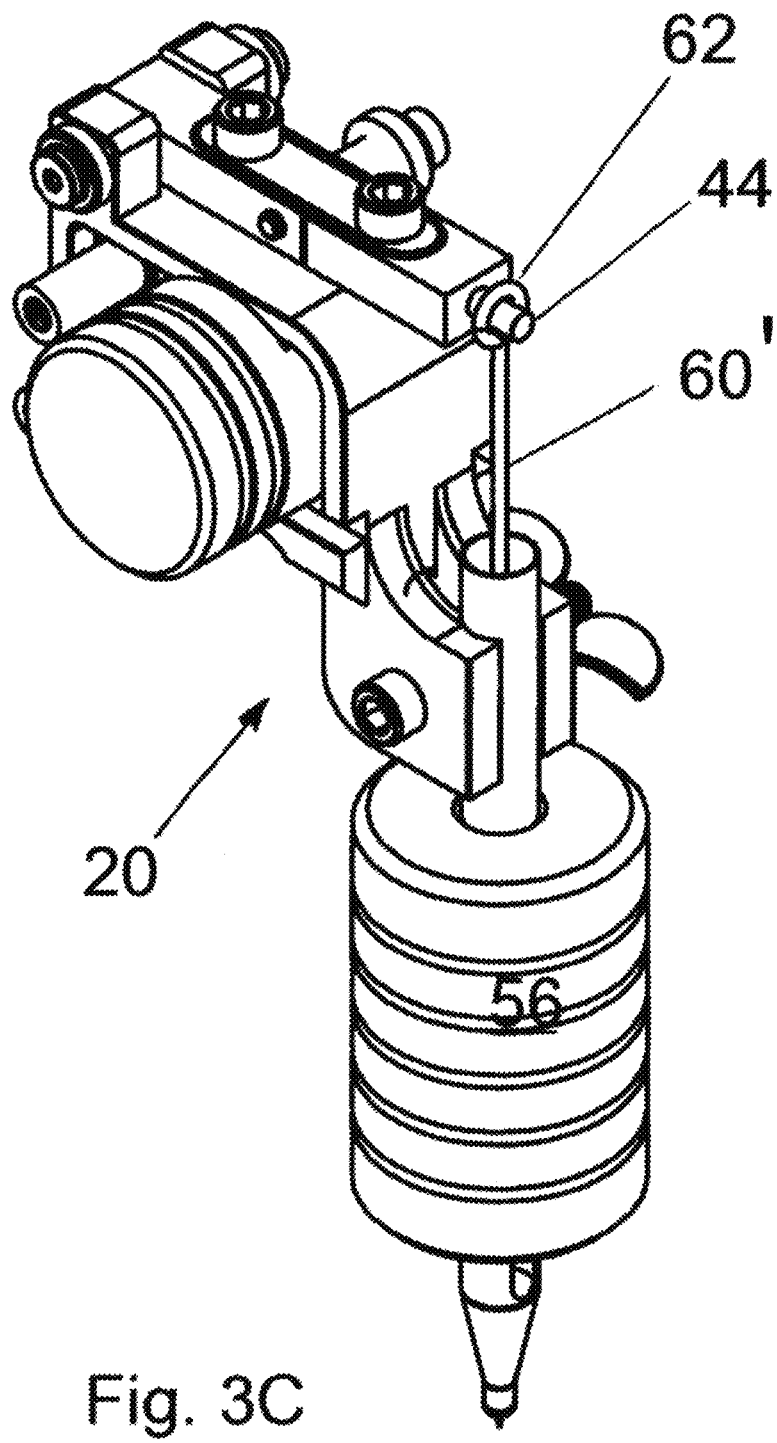
FIG. 3C is a right side perspective view of the first embodiment with the needle bar in place.

The basic operation of the tattoo machine assembly is best understood by reference to FIGS. 3A, 3B, 3C, 4, 4A, and 4B. As seen in FIG. 3C, needle bar 60 has a loop 62 which receives, and is moved by, nib 44. Needle bar 60' is guided by tube 57 of hand grip 56. Armature bar 40 is bifurcated into a front portion 42 with a protruding nib 44 and a rear portion 46. Rear portion 46 is attached to cam shaft 50 which is caused to oscillate by eccentric cam 48. Cam 48 is driven by rotary motor 52 to oscillate armature bar 40 between maximum position and minimum position (FIG. 3B). The tattoo needle bar 60' extends through handle grip tube 57 and is oscillated by the nib 44, similarly, through correspondingly minimum and maximum extending positions.

Steel spring plate 60 interconnects front portion 42 of armature bar 40 and rear portion 46 (FIG. 4) and determines the effective spring rate of armature bar 40. As mentioned earlier by way of example, not limitation, a series of seven steel plate springs, varying in thickness by 0.005 inch between 0.020 and 0.050 inches are provided to permit the spring rate of the armature bar to be adjusted for proper feel for the respective artist as well as accommodate different thicknesses and receptivities of skin. This spring rate variation alters the time the needle tip extends below the surface of the skin allowing additional time (a few micro-seconds) for the introduction of pigment belw the skin's surface. By increasing the "dwell time" for the ink pen tip below the skin's surface, the number of punctures needed can be reduced thereby limiting the damage to the skin resulting in accelerated healing of the tattoo site.

Various changes, alternatives, and modifications will become apparent to a person of ordinary skill in the art after a reading of the foregoing specification. It is intended that all such changes, alternatives, and modifications as fall within the scope of the appended claims be considered part of the present invention.

I claim:

1. In a tattoo machine assembly having an oscillating motor attached to a machine body to move a tattoo needle between a maximum and a minimum extended position, the improvement comprising:
   a) a bifurcated armature bar pivotably mounted atop said machine body, said bifurcated armature bar including a rear portion and a front portion pivotally secured to said rear portion; and,
   b) a steel plate spring means secured to said front and said rear portions of said armature bar to vary the spring rate afforded to said armature bar and, accordingly, to a tattoo needle secured thereto.

2. In the tattoo machine assembly of claim 1, the improvement comprising a plurality of steel plate springs each having a thickness that varies one from another, said plurality of steel plate spring means serving to vary the spring rate afforded to said armature bar.

* * * * *